United States Patent
Rezakhany

(10) Patent No.: US 8,679,462 B2
(45) Date of Patent: Mar. 25, 2014

(54) METHODS OF PREVENTING RESPIRATORY INFECTIONS

(76) Inventor: Saeed Rezakhany, San Jose, CA (US)

( * ) Notice: Subject to any disclaimer, the term of this patent is extended or adjusted under 35 U.S.C. 154(b) by 567 days.

(21) Appl. No.: 12/764,302

(22) Filed: Apr. 21, 2010

(65) Prior Publication Data

US 2010/0203166 A1   Aug. 12, 2010

Related U.S. Application Data

(63) Continuation-in-part of application No. 10/411,965, filed on Apr. 10, 2003, now abandoned.

(60) Provisional application No. 60/371,882, filed on Apr. 11, 2002.

(51) Int. Cl.
*A61Q 11/00* (2006.01)
*A61K 31/045* (2006.01)
*A61K 36/53* (2006.01)

(52) U.S. Cl.
USPC ............... 424/49; 424/434; 424/435; 424/58; 514/724

(58) Field of Classification Search
USPC .............................. 424/49, 434, 435; 514/724
See application file for complete search history.

(56) References Cited

U.S. PATENT DOCUMENTS

| | | | |
|---|---|---|---|
| 4,512,972 A | 4/1985 | Schmidt-Ruppin | |
| 5,002,970 A | 3/1991 | Eby, III | |
| 5,626,831 A | 5/1997 | Van Moerkerken | |
| 5,738,840 A * | 4/1998 | Richter | 424/53 |
| 5,900,401 A | 5/1999 | Kido et al. | |
| 6,107,281 A | 8/2000 | Jones et al. | |
| 6,121,315 A | 9/2000 | Nair et al. | |
| 6,165,494 A | 12/2000 | Picciano | |
| 6,365,624 B1 | 4/2002 | Davidson et al. | |
| 6,447,816 B1 | 9/2002 | Vail et al. | |
| 6,641,801 B1 | 11/2003 | Brown | |

OTHER PUBLICATIONS

Definition of Soft Palate, http://medical-dictionary.thefreedictionary.com/p/Soft%20palate, p. 1, retrieved Dec. 23, 2008.*
Gargle, http://www.thefreedictionary.com/p/gargle, Definition of Gargle, pp. 1-2, retrieved Dec. 23, 2008.*
Diagram of the Mouth, http://visual.merriam-webster.com/human-being/sense-organs/smell-taste/mouth.php, pp. 1-2, retreived Dec. 23, 2008.*
CliffNotes, http://www.cliffsnotes.com/WileyCDA/CliffsReviewTopic/Structure-of-the-Respiratory-System.
topicArticleId-22032,articleId-21997.html pp. 1-4, retrieved Dec. 22, 2008.*
Lambert Pharmacal. CO, So many times in a day in Danger, Life magazine Dec. 1937, pp. 1-3.*
Pfizer, Listerine Antiseptic Mouthwash, http://www.pfizerch.com/product.aspx?id=428 pp. 1-2.*
Fattah, E., The Frenzel Technique, Step-y-Step, pp. 1-8, 2001.*
eHow, How to Gargle, Feb. 1, 2001, pp. 1-2.*
McMilan et al., "Ordered nanoparticle arrays formed on engineered chaperonin protein templates," Nature Materials 1:247-252, Dec. 2002.
<www.listerine.com/history.aspx>.
Listerine® Mouthwash instructions on packaging.
[Target® Brand] Antiseptic Mouthwash instructions on packaging.
Scope® Mouthwash instructions on packaging.
Crest® Mouthwash instructions on packaging.
Biotene® Mouthwash instructions on packaging.
Definition of Soft Palate, <medical-dictionary.thefreedictionary.com/p/Soft%20palate>, p. 1, retrieved Dec. 23, 2008.
Gargle, <www.thefreedictionary.com/p/gargle>, pp. 1-2, retrieved Dec. 23, 2008.
Diagram of the Mouth, <visual.merriam-webster.com/human-being/sense-organs/smell-taste/mouth.php>, pp. 1-2, retrieved Dec. 23, 2008.
Listerine® Antiseptic Mouthwash [online], [retrieved May 3, 2005] <www.oral-care.com/conaffairs/listerine.shtml>.
Coolmint Listerine Antiseptic Mouthwash [online], [retrieved May 3, 2005] <www.oral-care.com/comaffairs/listerinecoolmint.shtml>.
Airborn Effervescent Health Formula Dietary Supplement Tablets [online], [retrieved May 3, 2005]. <www.drugstore.com/products/prod.asp?pid=76905&catid=382&trx=29384&tab=0#0>.

(Continued)

*Primary Examiner* — Lezah Roberts
(74) *Attorney, Agent, or Firm* — Moore Patents; David Dreyfuss; Cynthia R. Moore

(57) ABSTRACT

Methods for inhibiting the development of respiratory infections in humans are disclosed. One embodiment of the methods comprises pouring a predetermined amount of an oral rinse, capable of rendering ineffective a pathogen which has recently infected the respiratory tract, into the mouth of the human, agitating the oral rinse with air for a predetermined period in order to generate concentrated vapor of the oral rinse, stopping the agitating a plurality of times during which the head is tilted forward to allow the predetermined amount of an oral rinse to move away from the back of the mouth and throat, then exhaling before inhaling such that the concentrated vapor of the oral rinse is gently forced along with exhaled air from the throat thorough the nasopharynx and the nasal passages of the human, and then inhaling slowly to pass air over the oral rinse in the mouth such that concentrated vapor of the oral rinse is gently forced along with inhaled air through the larynx, over the vocal cords, and through the trachea to the lungs. The method is performed within about one hour after the human experiences the first minor symptom and before the onset of the first major symptom of infection of the respiratory tract.

13 Claims, No Drawings

(56) References Cited

OTHER PUBLICATIONS

Cold, Cough, and Sore Throats—prevention and treatment information [online], [retrieved Apr. 27, 2005], <www.mckinley.uiuc.edu/health-info/dis-cond/cold/cold-cough-sorethroat.html>.

Cold and Flu Guidelines: Influenza [online], [retrieved Apr. 27, 2005], <www.lungusa.org/site/pp. asp?o=dvLUKK90OE&b=35868>.

<en.wikipedia.org/wiki/Common-cold.

Wurges, J. The Gale Encyclopedia of Alternative Medicine "Eucalyptus," pp. 637-640, Dec. 2000.

U. of Minn., Dept. of Otolaryngology Health-Related Library, Swimmer's Ear and Itchy Ears, <www.med.umn.edu/otol/library/swimmers.htm>, Oct. 1997, pp. 1-2.

Amer. Acad. of Allergy, Asthma & Immunology, Understanding Allergic Diseases, <www.pfizerch.com/product.aspx?id=428> Apr. 2003, pp. 1-2.

Listerine, <en.wikipedia.org/wiki/Listerine>, Jan. 2004, pp. 1-3.

<www.cliffnotes.com/WileyCDA/CliffsReviewTopic/Structure-of-the-Respiratory-System.topicArticleId-22032,article21997.html>, pp. 1-4, retrieved Dec. 22, 2008.

\* cited by examiner

METHODS OF PREVENTING RESPIRATORY INFECTIONS

CROSS-REFERENCE TO RELATED APPLICATIONS

This application is a Continuation-in-Part Application claiming priority from U.S. patent application Ser. No. 10/411,965, filed Apr. 10, 2003, and further claiming priority from U.S. Provisional Patent Application No. 60/371,882, filed Apr. 11, 2002, both of which are incorporated herein by reference.

FIELD OF THE INVENTION

One or more embodiments of the present invention relate to the prevention of respiratory infections.

BACKGROUND

Respiratory infections, particularly upper respiratory infections ("URIs") are very common and cause substantial suffering and hundreds of millions of dollars of economic loss every year. The majority of the pathogens contributing to upper respiratory tract infections are spread through air and through direct contact by touching of hands to infected surfaces and then touching hands to eyes, nose, or mouth. The nasopharynx, nasal passages, and sinus cavities all play an important role in filtering and housing the majority of these pathogens.

No effective, easy to use, and widely accepted cure, treatment, remedy, and particularly no prevention has been found for upper respiratory infections. Stores are full of products that are alleged to reduce the severity of symptoms after infection has already developed. Numerous "home remedies," homeopathic products and treatments, and the like also exist. Many of these products offer little more than a placebo effect treatment, and the patient basically eventually fights the infection using internal infection-fighting resources. Vaccines exist for influenza. These are typically highly specific to a particular organism and must be newly developed each year for the strain or strains prevalent that year. Prescription medicines are also available to treat influenza, although the cost, need for a prescription, and associated time delays before beginning treatment have prevented the widespread use of such medicines.

Certain generally recommended hygiene practices can reduce the spread of URIs. These include washing hands frequently and thoroughly with soap and water; washing face, nose, eyes; not touching dirty hands to the eyes, nose, ears, mouth, and face; resting well; eating well; and exercising. At various times in the past, oral rinses (mouthwashes) have also been suggested to be beneficial for treating cold symptoms. However, such recommendations do not appear on current products, because efficacy has not been demonstrated, and manufacturers want to avoid accusations of false claims.

SUMMARY OF THE INVENTION

Methods for inhibiting the development of respiratory infections in humans are disclosed. One embodiment of the methods comprises pouring a predetermined amount of an oral rinse, capable of rendering ineffective a pathogen which has recently infected the respiratory tract, into the mouth of the human, agitating the oral rinse with air for a predetermined period in order to generate concentrated vapor of the oral rinse, stopping the agitating a plurality of times during which the head is tilted forward to allow the predetermined amount of an oral rinse to move away from the back of the mouth and throat, then exhaling before inhaling such that the concentrated vapor of the oral rinse is gently forced along with exhaled air from the throat thorough the nasopharynx and the nasal passages of the human, and then inhaling slowly to pass air over the oral rinse in the mouth such that concentrated vapor of the oral rinse is gently forced along with inhaled air through the larynx, over the vocal cords, and through the trachea to the lungs. The method is performed within about one hour after the human experiences the first minor symptom and before the onset of the first major symptom of infection of the respiratory tract.

DETAILED DESCRIPTION

Upper respiratory infections ("URIs") such as the common cold and influenza (the "flu") are generally preceded by one or more of a number of minor symptoms such as minor headaches, minor eye aches, minor ear aches, minor sore throat, minor body ache, minor nasal congestion, slight runny nose, minor cough, slight itching or scratchiness in the throat, itchiness in the ear, minor hoarseness, roughness in the eyes when moving the eyes or when blinking, sneezing, minor chills or shivers at normal room temperature, feeling abnormally warm at normal room temperature. These symptoms are characterized here as "minor" in the sense that they are just barely detectable and felt by the affected individual, they have typically just begun to be felt within the last hour or so, and they do not yet interfere significantly with normal daily activities. People generally ignore these symptoms, hoping they will just go away, or thinking that they may be caused by a minor allergy or irritation from dust or similar external cause. They wait for symptoms to develop into something more serious before beginning treatment. These symptoms can be called "major symptoms." Examples include sore throat, fever, muscle aches, serious headache, etc. These symptoms are characterized here as "major" in that they cause significant discomfort to the affected individual, persist for an extended period of time (hours to days or even weeks), cause a general feeling of illness, and interfere with normal daily activities including work, play, and sleep.

Treatment options for URIs are very limited. A variety of over-the-counter remedies are available, most of which have limited efficacy, and most URIs are basically allowed to run their course until the body's defense mechanisms eventually succeed in fighting off the infection. The present invention is directed to adapting some of the available over-the-counter products, specifically oral rinse products, to treatment before a URI has fully developed. This treatment, if practiced according to the methods disclosed herein, has surprisingly been found to consistently prevent the development of URIs.

An important aspect of the present invention is the commencement of treatment at the earliest possible time as soon as even one of the minor symptoms is felt. The human body is equipped with organs such as the tonsils and the nervous system, that give early warnings about the invasion of the respiratory tract by pathogens. This early warning initially produces minor symptoms that people tend to ignore. The inventor has discovered, however, that treatment advantageously begins within the first hour or so from the onset of the first minor symptom. If one waits longer, then it can become progressively more difficult to prevent the development of the major symptoms. The goal is to render ineffective the pathogen(s) causing the infection as soon as their presence is detected and before they have a chance to multiply significantly. The method becomes less effective or ineffective if treatment is delayed until the onset of the first major symptom.

According to one or more embodiments of the present invention, an over-the-counter oral rinse or mouthwash is used. This is generally an anti-microbial solution. Reported "active" ingredients vary from product to product. A typical product includes one or more of thymol, eucalyptol, methyl salicylate, menthol, and iodine. Most products also contain alcohol which can also be an "active" ingredient for use with the present invention. A specific example composition comprises "active ingredients" thymol 0.064%, eucalyptol 0.092%, methyl salicylate 0.060%, and menthol 0.042%; together with "inactive ingredients" water, alcohol 26.9%, benzoic acid, poloxamer 407, and caramel.

According to one or more embodiments of the present invention, immediately after detecting one or more of the minor symptoms described above, approximately 1 tablespoon (15 ml) of an oral rinse is poured into the mouth. The mouth is quickly rinsed. Next, concentrated vapors or volatile components of the oral rinse are generated by agitation of air with the oral rinse. For example, such concentrated vapors can be generated by gargling: the head is tilted back so that the liquid goes to the back of the mouth and throat area, then gargling is started. For the present purposes, "gargling" consists of slowly bubbling air by exhaling through liquid in the back of the mouth and throat area. As another example, concentrated vapors can be generated by vigorously swishing the oral rinse around in the mouth and through the teeth. The concentrated vapor generation should be performed for approximately 40 seconds. At least three times during that time, the head is tilted forward slightly so that the liquid comes away from the back of the throat, then the concentrated vapors of the oral rinse present in the throat area is slowly forced out through the nasopharynx and the nasal passages by exhaling through the nose. This exhaling is performed without first inhaling as would normally be done when gargling repeatedly. After exhaling, and before resuming the concentrated vapor generation, additional air is inhaled to bring vapors into the lungs. This is preferably done by slowly inhaling through the mouth; air is passed over the oral rinse which is, at that point in time, located toward the front of the mouth. This inhaling brings air concentrated with vapor from the oral rinse through the larynx, over the vocal cords, and through the trachea into the lungs, thereby treating the remainder of the respiratory system that was not fully exposed to concentrated vapor during the concentrated vapor generation and subsequent exhalation. Also at some point, before, during, or after the above steps, the oral rinse should be swished around the mouth several times to thoroughly disinfect the mouth.

After the above steps are complete, including the mouth rinsing, the oral rinse should be emptied out from the mouth. While the ingredients are generally non-toxic to humans in the quantities typically used, manufacturers generally recommend against swallowing the oral rinse into the stomach. The mouth can then be rinsed with water so that little or no oral rinse remains in the mouth.

If one or both of the nasal passages are congested and thus do not pass air easily, then the entire method should be repeated when the passages open up or become less congested. Of course, it is best to begin treatment before nasal passages become congested, but there are situations in which the passages may already be clogged due to allergies, environmental irritants, or excessive delay before first treatment.

There are two important features of the above-described methods that are not present in any prior art description of the use of oral rinses. One is the use for the prevention of URIs by treating before any major symptoms develop. The second is the treatment of the entire respiratory system including the mouth, nose, nasal passages, nasopharynx, larynx, trachea, and lungs with either the liquid or concentrated vapors from the oral rinse. This treatment of the entire respiratory system is never an accidental byproduct of any prior art methods nor is it inherent in gargling as it is commonly practiced or as recommended by manufacturers of oral rinse products. The current focus of advertising and product literature for oral rinses is on oral and dental health, treating such conditions as gingivitis and halitosis (bad breath). Directions often do not even mention gargling, focusing instead on treating just the mouth with the liquid product. It requires the novel method steps of the present invention embodiments to adequately treat the entire respiratory system with concentrated vapor.

According to one or more embodiments of the present invention, the complete method described above is repeated at least four times per day (i.e., every 4-6 hours) from the onset of the first symptom until at least two treatments after the last symptom is detected. This is the recommended minimum frequency and duration of treatment. If initial minor symptoms become more pronounced, then treatment frequency should increase to approximately every 30-60 minutes during waking hours. Also, if exposed to other infected persons such as family members, co-workers, classmates, etc. with known symptoms of a URI, or if there is a known URI epidemic in progress, then the frequency of treatment can similarly be increased to approximately every 30-60 minutes during waking hours.

As a further preventative measure, during the cold and flu season, even if no symptom exists and no suspected exposure to infected persons has occurred, the method described above can be performed two or preferably three times a day, once right after rising in the morning, midday (if possible), and once again before going to bed at night.

Also, during the cold and flu season, within one hour after meeting with people or traveling through crowded places, the method can be performed, again as a preventive measure. If the duration of exposure (for example, during travel or a public meeting) is longer than about two hours, then the method can advantageously be performed at least once during exposure and again after exposure. If it is suspected that specific exposure to an infected person is occurring, then the method can be performed approximately every 60 minutes throughout the exposure.

The 15 ml of oral rinse and 40 seconds duration of agitating with air are the amount and duration suitable for a healthy adult of medium size. The amount and duration can vary with the age and size of the person, as well as with other factors such as tolerance for the ingredients in the oral rinse. In general, the amount of oral rinse used should both facilitate easy gargling or agitating and allow the liquid to be moved to the front of the mouth for the exhaling and inhaling steps.

The methods as described above are focused on the prevention of the development of any major symptoms. However, in accordance with one or more embodiments of the present invention, a URI which has progressed past the minor symptom stage can still be beneficially treated to reduce the severity and duration of the major symptoms and the prevention of secondary infections. The recommended treatment frequency in this case is the same as for a person exposed to other infected individuals, i.e., every 30-60 minutes during waking hours.

The methods of this invention should not be used as a substitute for other established procedures known to benefit health and prevent of the spread of respiratory infections.

These other procedures include washing hands frequently and thoroughly with soap and water; washing face, nose, eyes; not touching dirty hands to the eyes, nose, ears, mouth, and face; resting well; eating well; and exercising. The methods presented here should be used in conjunction with these other good health habits.

While testing has been conducted with regard to common URIs, the methods of the present invention can also be beneficial for most, if not all, other types of respiratory infections.

EXAMPLES

The inventor has experimented with the methods on himself and has asked several relatives, friends, and acquaintances to do the same. The experiments were all successful in preventing major cold symptoms, namely high fever, lack of energy, major congestion, body ache, having to stay in bed, etc.

In order to achieve success with the methods, each person reported that they had to follow the methods rigorously to achieve successful results. That is, very soon after feeling initial minor symptoms, one needs to administer the effective formula according to the method presented above.

As of the April 2010, 26 people were asked to try the methods. All reported success. Among these, 14 were male and 12 were female. Their ages ranged from 5 to 83. The time span for the experiments has been approximately 12 years (1998-2010). At least 12 out of 26 of these subjects have participated on a regular basis. At least since 2003, they have participated during every cold and flu season (approximately October through April). Typically, during each cold and flu season, each subject experienced about 15 cold or flu "attacks," i.e., some of the initial minor symptoms of the possible onset of a cold or flu. Each time, and for each subject, if the method was followed accurately, major symptoms did not follow (100% success). However, not every subject followed the method accurately with each attack. Also, sometimes a reduced-version of the method was followed, for example, to reduce the time required during each application of the method and/or to reduce the unpleasantness from the bad taste of the oral rinse. In these cases, the desired results were not obtained, and at least some major symptoms of cold or flu followed. The lesson learned from these years of experimentation has been that, if the method is followed rigorously, no major symptom of cold or flu follows the initial symptoms. On the other hand, if the method is not followed rigorously, at least some major symptoms do follow. Therefore, the failure rate was zero for all subjects if the method was followed properly. While the testing remains limited to a relatively small number of subjects, the unexpectedly high success rate is indicative of the effectiveness of the method and the novelty of the method compared to all prior art uses of oral rinses to treat symptoms of URIs.

What is claimed is:

1. A method for treating a human, the method comprising:
   (a) pouring a predetermined amount of an oral rinse, capable of rendering ineffective a pathogen which has infected the respiratory tract, into the mouth of the human,
   (b) agitating said oral rinse with air for a predetermined period in order to generate concentrated vapor of the oral rinse,
   (c) stopping said agitating, tilting the head forward to allow said predetermined amount of an oral rinse to move away from the back of the mouth and throat, then exhaling before inhaling such that the concentrated vapor of the oral rinse is gently forced along with exhaled air from the throat through the nasopharynx and the nasal passages of the human,
   (d) inhaling slowly to pass air over the oral rinse in the mouth such that concentrated vapor of the oral rinse is gently forced along with inhaled air through the larynx, over the vocal cords, and through the trachea to the lungs, and
   (e) repeating steps (c) and (d) at least one additional time after additional agitating.

2. The method of claim 1, wherein the method is started within about one hour after said human experiences the first of a set of minor symptoms comprising minor headaches, minor eye aches, minor ear aches, minor sore throat, minor body ache, minor nasal congestion, slight runny nose, minor cough, slight itching or scratchiness in the throat, itchiness in the ear, minor hoarseness, roughness in the eyes when moving the eyes or when blinking, sneezing, minor chills or shivers at normal room temperature, or feeling abnormally warm at normal room temperature.

3. The method of claim 1, wherein the method is started before the onset of the first major symptom of infection of the respiratory tract.

4. The method of claim 1, wherein the method is repeated at intervals of four to six hours during waking hours until at least two treatments after the last minor symptom is experienced.

5. The method of claim 1, wherein the method is repeated at intervals of about 30-60 minutes during waking hours until at least two treatments after the last minor symptom is experienced and throughout any period during which the human is exposed to other humans known or suspected of being infected by said pathogen.

6. The method of claim 1, wherein the method is performed two or three times per day during the cold and flu season.

7. The method of claim 1, wherein the method is performed within one hour after the human meets other individuals during cold and flu season or within one hour after the human is exposed to crowds during cold and flu season.

8. The method of claim 7, wherein the duration of the meeting or exposure to crowds is longer than about two hours, and wherein the method is performed at least once during the meeting or exposure to crowds and once afterwards.

9. The method of claim 1, wherein the method is performed approximately every hour while the human is exposed to a person who is known to be infected with said pathogen.

10. The method of claim 1, wherein the active ingredient of said oral rinse comprises one or more of thymol, eucolyptol, methyl salicylate, iodine, and ethanol.

11. The method of claim 1, wherein steps (c) and (d) are repeated at least three times in total.

12. The method of claim 1, wherein said pathogen is a pathogen which has infected the upper respiratory tract.

13. The method of claim 1, wherein said agitating comprises gargling.

* * * * *